United States Patent
Fish et al.

(10) Patent No.: US 10,962,523 B2
(45) Date of Patent: Mar. 30, 2021

(54) APPARATUS AND METHODS FOR MEASURING AN ELECTRICAL CURRENT

(71) Applicant: Oxford Nanopore Technologies Ltd., Oxford (GB)

(72) Inventors: David A. Fish, Redhill (GB); Steven Paul White, Oxford (GB)

(73) Assignee: Oxford Nanopore Technologies Ltd., Oxford (GB)

(*) Notice: Subject to any disclaimer, the term of this patent is extended or adjusted under 35 U.S.C. 154(b) by 511 days.

(21) Appl. No.: 15/573,332

(22) PCT Filed: May 9, 2016

(86) PCT No.: PCT/GB2016/051319
§ 371 (c)(1),
(2) Date: Nov. 10, 2017

(87) PCT Pub. No.: WO2016/181118
PCT Pub. Date: Nov. 17, 2016

(65) Prior Publication Data
US 2018/0143178 A1    May 24, 2018

(30) Foreign Application Priority Data
May 11, 2015 (GB) .................................... 1508003

(51) Int. Cl.
*G01N 33/48* (2006.01)
*G01N 33/50* (2006.01)
(Continued)

(52) U.S. Cl.
CPC ... *G01N 33/48728* (2013.01); *G01R 19/0053* (2013.01); *G01N 33/48721* (2013.01)

(58) Field of Classification Search
CPC ....... G01N 33/48728; G01N 33/48721; G01R 19/0053
See application file for complete search history.

(56) References Cited

U.S. PATENT DOCUMENTS 6,627,067 B1    9/2003    Branton et al.
6,723,814 B2    4/2004    Meier et al.
(Continued)

FOREIGN PATENT DOCUMENTS

WO    WO 2008/102120 A1    8/2008
WO    WO 2013/057495 A2    4/2013
(Continued)

OTHER PUBLICATIONS

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

(Continued)

*Primary Examiner* — Russell S Negin
(74) *Attorney, Agent, or Firm* — Wolf, Greenfield & Sacks, P.C.

(57) ABSTRACT

Arrangements are disclosed for measuring small electrical currents with high sensitivity, for example in the context of sensing molecular entities, for example via interactions between the molecular entities and a membrane protein inserted in an amphiphilic membrane. In one arrangement there is provided a current sensing circuit (52) configured to integrate the current output by a sensor element (56) during each of a plurality of sensing frames (62). In each sensing frame (62) first and second analogue samples of the integral are taken during first and second time windows (71,72). A readout circuit (54) processes the first and second analogue samples to output a digital output signal representing the current output by the sensor element (56). The processing comprises analogue to digital conversion processing and output processing. The output processing is performed exclusively during periods outside of the first and second time windows.

23 Claims, 7 Drawing Sheets

(51) Int. Cl.
*G01N 33/487* (2006.01)
*G01R 19/00* (2006.01)

(56) References Cited

U.S. PATENT DOCUMENTS

| | | | |
|---|---|---|---|
| 8,698,481 | B2 | 4/2014 | Lieber et al. |
| 8,828,211 | B2 | 9/2014 | Garaj et al. |
| 2007/0072169 | A1 | 3/2007 | Peyvan et al. |
| 2009/0026350 | A1 | 1/2009 | Leijssen et al. |
| 2011/0053284 | A1 | 3/2011 | Meller et al. |
| 2012/0107802 | A1 | 5/2012 | Stoddart et al. |
| 2012/0160681 | A1* | 6/2012 | Davis ............ C12Q 1/6869 204/452 |
| 2012/0222958 | A1* | 9/2012 | Pourmand ........ G01N 33/48721 204/451 |
| 2013/0244340 | A1* | 9/2013 | Davis ............ C12Q 1/6874 436/501 |
| 2013/0309776 | A1 | 11/2013 | Drndic et al. |
| 2014/0027287 | A1* | 1/2014 | Peng ............ B03C 5/026 204/601 |
| 2014/0174927 | A1 | 6/2014 | Bashir et al. |
| 2014/0176963 | A1* | 6/2014 | Kemp ............ G01B 9/02048 356/497 |
| 2014/0186823 | A1 | 7/2014 | Clarke et al. |

FOREIGN PATENT DOCUMENTS

| | | |
|---|---|---|
| WO | WO 2013/098561 A1 | 7/2013 |
| WO | WO 2013/098562 A2 | 7/2013 |
| WO | WO 2013/153359 A1 | 10/2013 |
| WO | WO 2014/064449 A1 | 5/2014 |

OTHER PUBLICATIONS

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Langecker et al., Synthetic lipid membrane channels formed by designed DNA nanostructures. Science. Nov. 16, 2012;338(6109):932-6. doi: 10.1126/science.1225624.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Nucleobase recognition in ssDNA at the central constriction of the alpha-hemolysin pore. Nano Lett. Sep. 8, 2010;10(9):3633-7. doi: 10.1021/nl101955a.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

* cited by examiner

APPARATUS AND METHODS FOR MEASURING AN ELECTRICAL CURRENT

RELATED APPLICATIONS

This application is a national stage application under U.S.C. § 371 of PCT International Application No. PCT/GB2016/051319, filed May 9, 2016, which claims foreign priority benefits under 35 U.S.C. § 119(a)-(d) or 35 U.S.C. § 365(b) of United Kingdom application number 1508003.9, filed May 11, 2015, the contents of each of which are incorporated herein by reference in their entireties.

The invention relates to measuring small electrical currents with high sensitivity, particularly but not exclusively in the context of sensing molecular entities, for example via interactions between the molecular entities and a sensor comprising a membrane protein inserted in an amphiphilic membrane.

It is known to sense molecular entities using a membrane protein inserted in an amphiphilic membrane. Interactions between the molecular entities and the membrane protein can cause characteristic modulations of an electrical signal appearing across the amphiphilic membrane. For example an ionic current flowing through a membrane protein that is a protein pore can be modulated by the interactions. By monitoring an electrical signal appearing across the amphiphilic membrane it is possible to detect the characteristic modulations and thereby sense the molecular entities. A variety of technologies have been proposed based on this principle, one example being disclosed in WO-2008/102120.

Sensing of molecular entities using this technique provides a method of identifying single molecules and molecular entities directly, without the need for fluorescent labelling and detection. There are a wide range of possible applications, such as sequencing of DNA or other nucleic acids; sensing of chemical or biological molecules for security and defense; detection of biological markers for diagnostics; ion channel screening for drug development; and label free analysis of interactions between biological molecules.

The currents that are detected are typically in the range 20 pA to 100 pA for DNA sequencing and with an open pore the currents are in the range 50 pA to 500 pA. The electronic detection of such currents is challenging. A multi-channel device may be employed in conjunction with an array of sensors. The device may be implemented using Application Specific Integrated Circuits (ASICs).

Sensitive current measurements are also required in other applications. For example, medical X-ray detectors are known in which charge created by X-ray quanta in direct and indirect conversion materials is detected. Such detectors also typically use ASICs and the minimum charge detection levels may be around 10000 electrons with about 1000 electrons of RMS noise. The X-ray detectors may operate by accumulating charge on a capacitance. The charge may be accumulated over a period of milliseconds for example. The accumulated charge may be read out into a charge amplifier in a few micro-seconds. In configurations of this type current levels are therefore in the nanoampere region. X-ray detectors employing thousands of sensing channels are known.

The charge levels seen in known nanopore sequencing applications are similar to those seen in known X-ray detectors. Similar noise levels are also required, typically equivalent to about 2 pA RMS current noise at 10 kHz sampling.

FIG. 1 shows an example current measurement apparatus configured to measure a current flowing through a nanopore. Corresponding arrangements, adapted as appropriate, may be provided for use in medical X-ray detectors or in other charge or current measurement devices.

The example apparatus comprises a charge integrating amplifier 12 which acts to integrate charge flowing through a nanopore represented by a resistor 10. A 50 pA current will generate a voltage of about 50 mV over 100 μs with the component values shown in the figure. After 100 μs the circuit is reset with a switch (not shown) on the integrating capacitance (the 100 fF capacitance in FIG. 1). FIG. 2 shows schematically how the voltage output rises as a function of time during the integration process.

The intrinsic noise performance can be analysed approximately as follows. FIG. 3 shows the main noise sources in the apparatus of FIG. 1. The resistor $R_{PORE}$ (having resistance $R_{PORE}$) represents the resistance of the nanopore. Noise in the resistor is represented by $V_{NPORE}$. $R_{PORE}$ will typically be in the range of 3 G to 20 GOhms or higher and will produce white noise $V_{NPORE}$ proportional to $\sqrt{4k_B T R_{PORE}}$, where $k_B$ is Boltzmann's constant and T is temperature. The amplifier noise source is shown as $V_{NAMP}$ and will typically be around 1 μV/√Hz at 1 Hz down to the white noise floor of 3 nV/√Hz above 100 kHz for a CMOS integrated amplifier. An important component is the capacitance of the amphiphilic membrane (which may be a bi-lipid layer), marked as $C_{BL}$. $C_{BL}$ is relatively large, typically around 30 pF for example. Finally the electrode resistance $R_{ELE}$ and associated noise $V_{NELE}$ are marked. $R_{ELE}$ may typically have a value of around 4 kOhms.

Although the nanopore resistance $R_{PORE}$ is very high it is heavily filtered by the capacitance $C_{BL}$ and its contribution to the overall RMS noise is negligible except at very low frequencies. The amplifier noise $V_{NAMP}$ and the electrode resistance noise $V_{NELE}$ are the dominant contributions because they are amplified by the ratio of the capacitance $C_{BL}$ to the capacitance $C_{FB}$ of the integrating capacitor 12. Typically this ratio is about 300.

FIG. 4 shows the noise spectrum at the output of the charge integrating amplifier 12. The RMS current noise under these conditions is about 5 pA RMS, which is relatively high. The RMS current noise can be reduced by applying known filtering techniques. For example, by applying correlated double sampling (CDS) and low pass (LP) filtering to the arrangement of FIG. 3 it is possible to reduce the noise level down to about 1.4 pA, which is acceptable for many applications, including detecting biological molecules in nanopores. The correlated double sampling has the effect of a high pass filter, so the combination is a band-pass filter at the sampling rate (or integration period) of the circuit. FIG. 5 shows the noise spectrum after the filtering has been carried out. FIG. 5 shows that it is possible in principle to achieve the required noise levels in the presence of intrinsic noise sources of the type discussed above. In practice, however, other noise sources exist and the low pass filtering and correlated double sampling are not always adequate to reach the required noise performance.

It is an object of the invention to at least partially address one or more of the problems discussed above. It is a particular object of the invention to reduce the level of noise in sensitive current measurements, especially in the context of sensing molecular entities via their interactions with a sensor element.

According to an aspect of the invention, there is provided a current measuring apparatus for measuring an electrical current output by a sensor element, the current measuring apparatus comprising: a current sensing circuit configured to integrate the current output by the sensor element during each of a plurality of sensing frames and, in each sensing frame, to obtain a first analogue sample of the integral during a first time window in the sensing frame and a second analogue sample of the integral during a second time window in the sensing frame, the second time window being later than the first time window in each sensing frame; and a readout circuit configured to process the first and second analogue samples in order to output a digital output signal representing the current output by the sensor element between the first and second time windows in each sensing frame, the processing comprising analogue to digital conversion processing to obtain the digital output signal and output processing to output the digital output signal, wherein: the readout circuit is configured to perform the output processing exclusively during periods outside of the first and second time windows.

The inventors have recognised that operations associated with the readout circuit can, if counter measures are not taken, cause significant amounts of noise to couple into the sensitive circuitry (e.g. amplifiers) of the integrating amplifier circuit. These noise coupling effects may arise for example from Mixed Signal (MS) circuitry (i.e. circuitry dealing with both analogue and digital signals). The noise can couple to the integrating amplifier circuit through the silicon substrate of the ASIC, for example, where the current sensing circuit and readout circuit are implemented on the same ASIC. The noise may also couple through power supplies or reference voltage supplies, where these are provided. The noise coupling is particularly problematic for operations which require a relatively high power, such as the output processing.

According to the present embodiment, the effects of noise associated with processing of the readout circuit are greatly reduced or eliminated by arranging for at least the output processing of the readout circuit to operate only outside of first and second time windows used to obtain the analogue samples which are used to derive the current measurement. Thus, while the noise from the output processing can contribute temporarily to the output from the integrating amplifier circuit, AC components of the noise, which in many situations will be the only or dominant contributions to the noise, will tend to have little or no effect on the trajectory of the integration process after the noise has stopped. By arranging for the first and second analogue samples to be obtained outside of the period when at least the output processing of the readout circuit is operational, the influence of noise from the readout circuit on the current measurement is greatly reduced or eliminated.

In an embodiment, the readout circuit is configured to perform all digital operations of the analogue to digital conversion processing exclusively during periods outside of the first and second time windows. Digital operations of the analogue to digital processing normally involve lower powers than the output processing but may still contribute significantly to noise. Avoiding performing such operations during the first and second time windows may further reduce the level of noise in the current measurements.

In an embodiment, all operations of the readout circuit are performed exclusively during periods outside of the first and second windows. Operations of the readout circuit other than the output processing and the digital operations of the analogue to digital processing normally involve lower powers but may still contribute to noise. Avoiding all operations of the readout circuit during the first and second time windows may further reduce the level of noise in the current measurements.

In an embodiment, the readout circuit is configured to perform a portion or all of one or more of the following during one or more of the sensing frames: the output processing, all digital operations of the analogue to digital conversion processing, all operations of the readout circuit. In an embodiment, in respect of the current output by the sensor element in each sensing frame the readout circuit is configured to perform the output processing (and, optionally, other processing) during one or more periods outside of that sensing frame. In an embodiment the one or more periods comprise a period during integration of the current output by the sensor element in one or more later sensing frames.

Performing the output processing (and, optionally, other processing) during the integration (but outside of the first and second time windows) typically provides a much longer operational period than alternative approaches which only allow use of time periods outside of the integration (e.g. in the reset periods). To achieve still longer operational periods for the output processing (and, optionally, other processing), the reset period may be used in addition.

It is often desirable to carry out many measurements of current in parallel, which requires high readout rates in order to be practical. The present invention makes it possible to achieve the required high sensitivities and high readout rates because the period outside of the first and second time windows can be made relatively long without increasing the size of the sensing frames themselves. This is because the period outside of the first and second time windows can be a large fraction of the duration of each sensing frame, or even larger than the duration of each sensing frame (where both the periods between first and second time windows within each sensing frame and the periods between the second time windows of each sensing frame and the first time windows of each subsequent sensing frame are used). Considerable time is therefore available to complete the operations of the readout circuit that may be required for reading out from many sensor elements or groups of sensor elements without introducing extra delay between the sensing frames.

In an embodiment the current measuring apparatus will be implemented in a device that is intended to be disposable. In this situation it will be desirable to provide a low pin count to enable repeatable connections to the host device e.g. USB connection. A low pin count will increase the need to provide significant digital circuitry on the ASIC for complex readout circuit functionality, such as may be required in nanopore applications. Embodiments of the invention are particularly advantageous in this situation where the significant digital circuitry will tend to increase the potential sources of noise.

In an embodiment, the sensor elements are each arranged to support an amphiphilic membrane in which a membrane protein is capable of insertion, and the interaction between the molecular entity and the sensor element is an interaction between the molecular entity and the membrane protein in the amphiphilic membrane. Embodiments of the invention are well suited to applications of this type where the currents being measured may be extremely small and where many thousands of measurements may need to be made in parallel.

According to an alternative aspect, there is provided a current measuring apparatus for measuring an electrical current output by a sensor element, the current measuring apparatus comprising: a current sensing circuit configured to integrate the current output by the sensor element during each of a plurality of sensing frames and, in each sensing frame, to obtain a first analogue sample of the integral during a first time window in the sensing frame and a second analogue sample of the integral during a second time window in the sensing frame, the second time window being later than the first time window in each sensing frame; and a readout circuit configured to process the first and second analogue samples in order to output a digital output signal representing the current output by the sensor element between the first and second time windows in each sensing frame, the processing comprising analogue to digital conversion processing to obtain the digital output signal and output processing to output the digital output signal, wherein: the readout circuit is configured to perform the output processing exclusively during periods outside of the first and second time windows.

Embodiments of the invention will now be described, by way of example only, with reference to the accompanying drawings in which corresponding reference symbols indicate corresponding parts, and in which.

Figure 7:
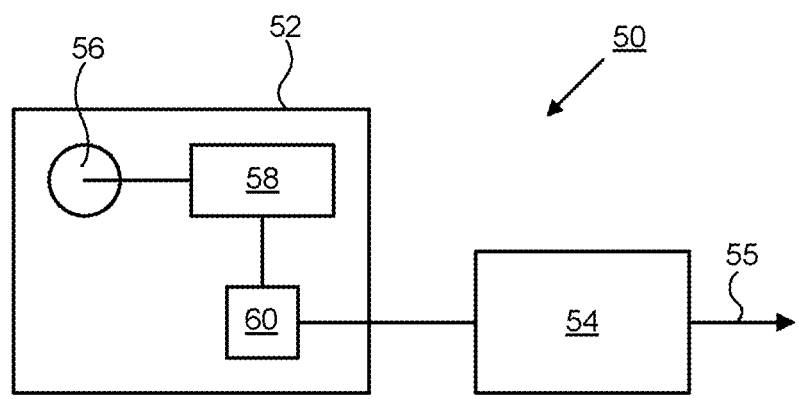
FIG. 7 is a schematic depiction of an apparatus for measuring an electrical current according to an embodiment.

In an embodiment, there is provided an apparatus 50 for measuring an electrical current output by a sensor element 56. An example configuration for the apparatus is shown in FIG. 7. In an embodiment the sensor element 56 is configured to sense occurrences of a physical event or phenomenon by outputting an electrical signal in the form of an electrical current. The physical event or phenomenon may be an interaction between a molecular entity and the sensor element 56, for example an interaction between a molecular entity and a membrane protein such as a protein pore.

Figure 1:
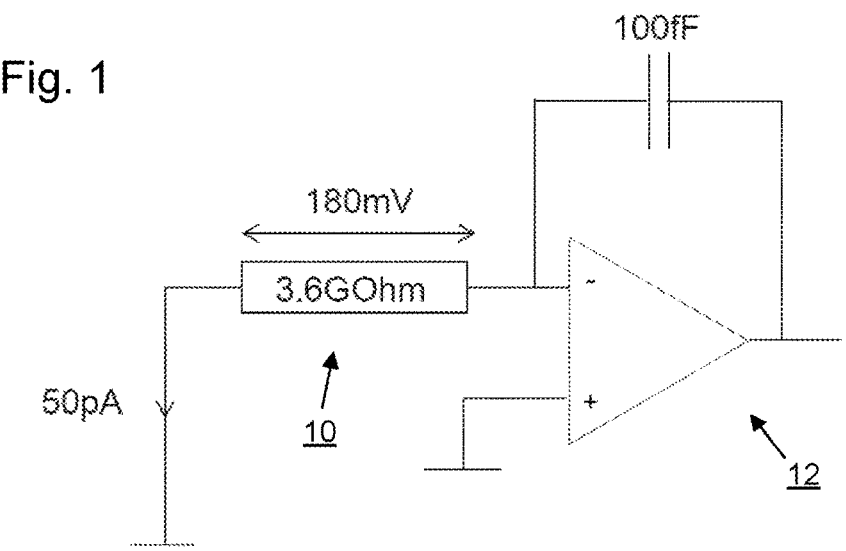
FIG. 1 is an example prior art circuit for measuring a current using a charge integrating amplifier.
Figure 2:
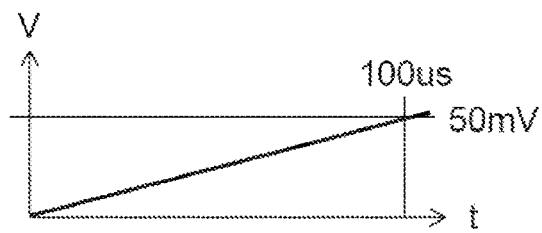
FIG. 2 is a graph showing schematically how the voltage output of the circuit of FIG. 1 rises with time during an integration process.
Figure 3:
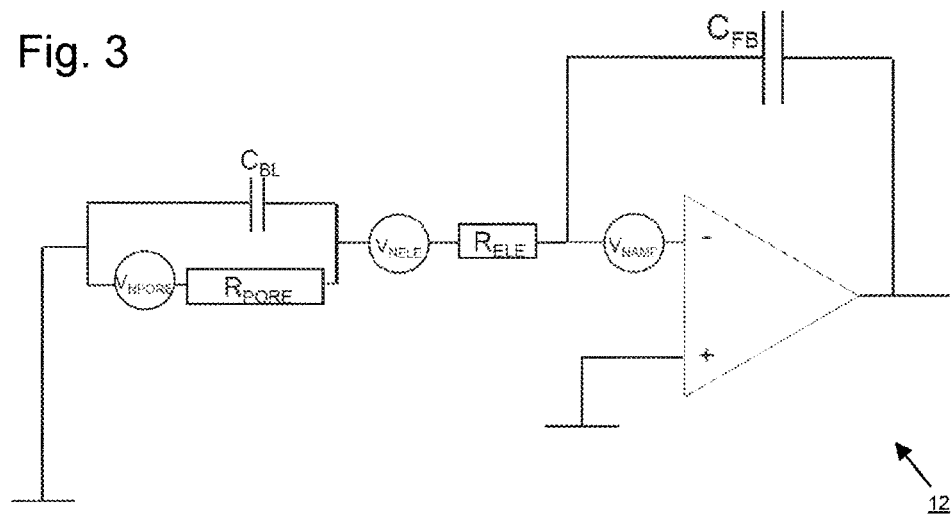
FIG. 3 is schematic illustration of sources of noise in the circuit of FIG. 1.
Figure 4:
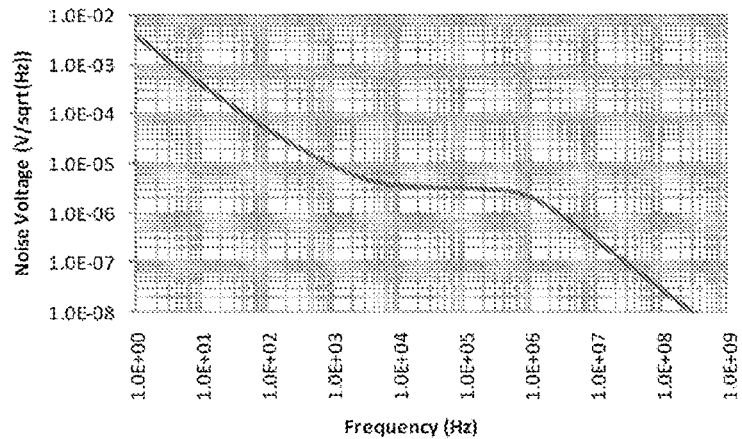
FIG. 4 is a graph showing an example noise spectrum for the circuit of FIG. 1.
Figure 5:
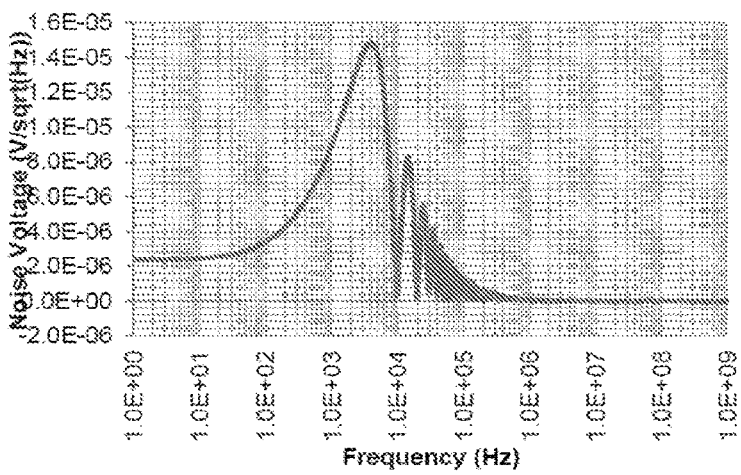
FIG. 5 is a graph showing an example noise spectrum for the circuit of FIG. 1 after low pass filtering and correlated double sampling is applied to the circuit.
Figure 6:
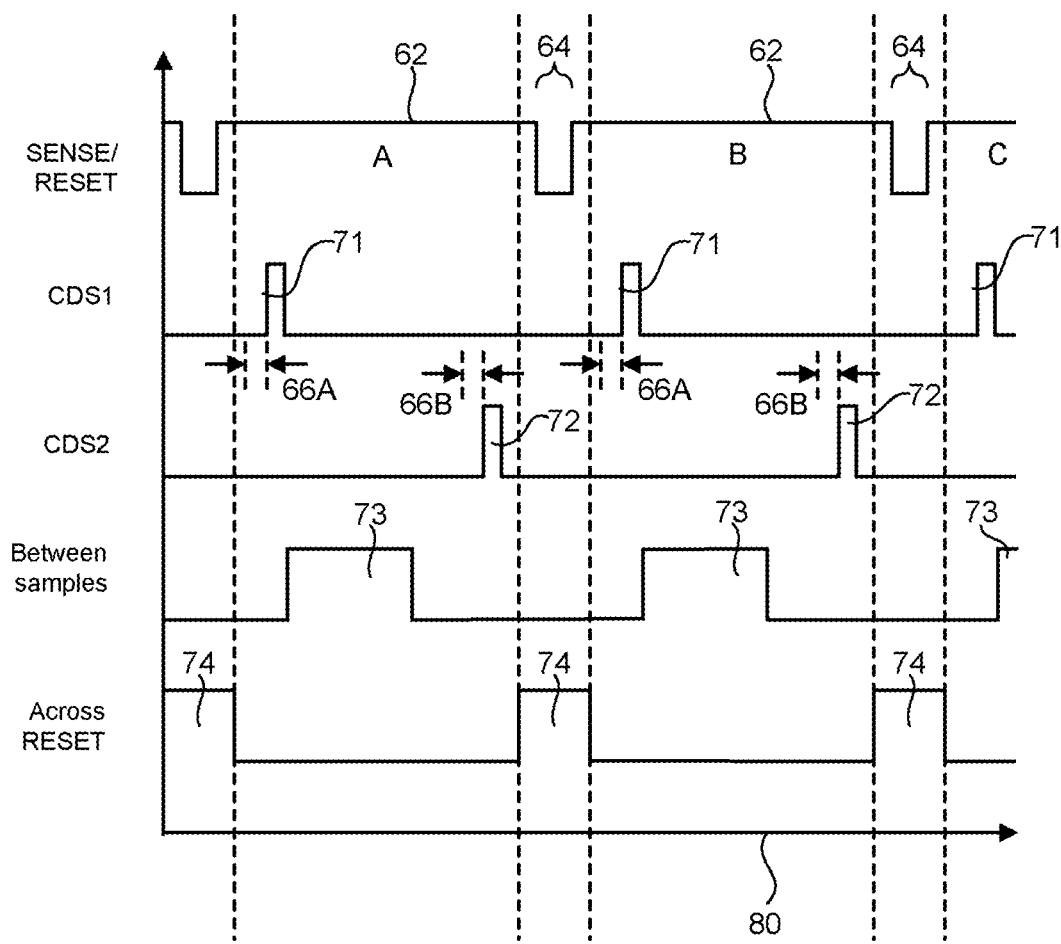
FIG. 6 is a set of graphs illustrating example relative timings of operations in an apparatus according to an embodiment.
Figure 8:
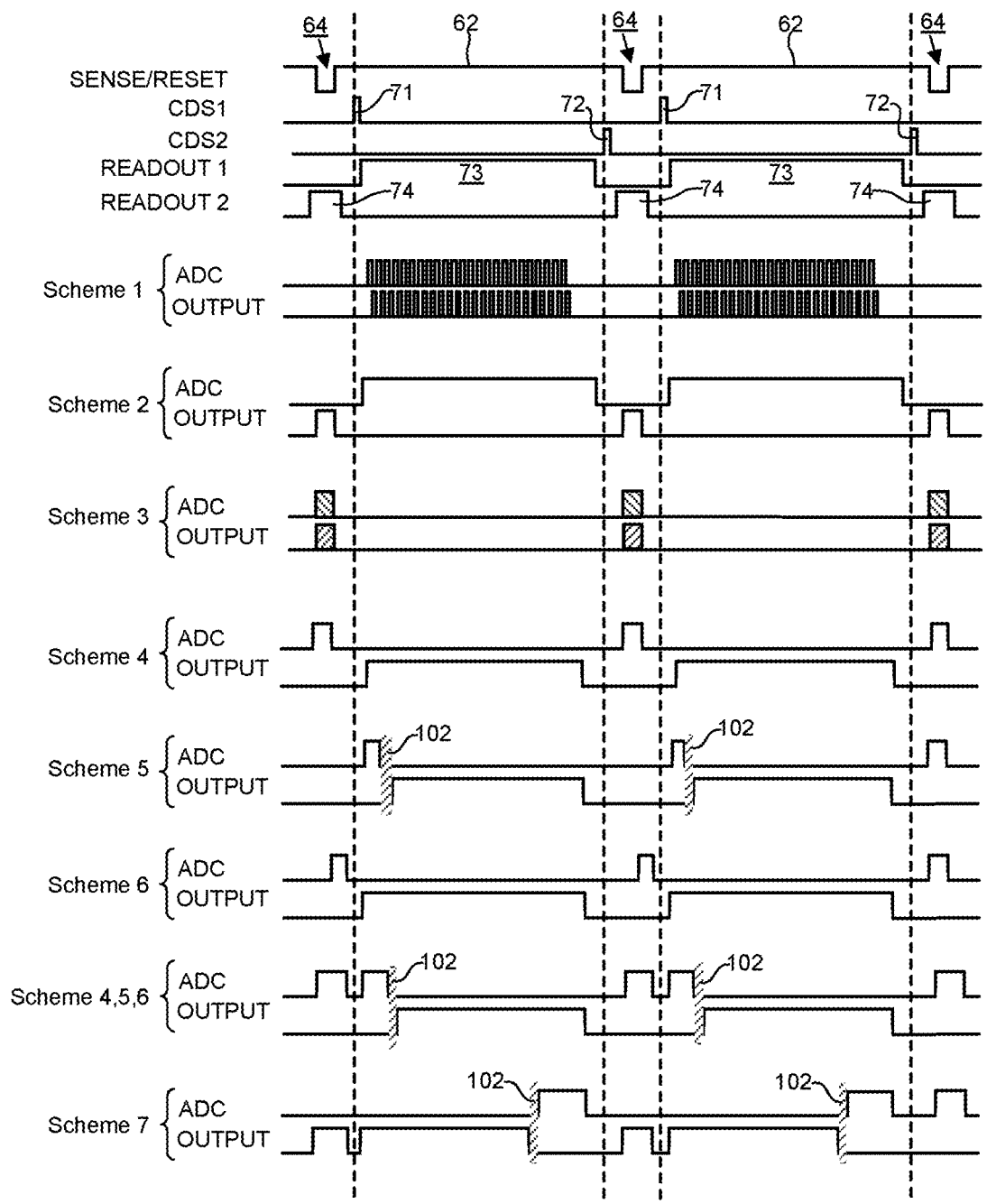
FIG. 8 is a set of graphs comparing different timing schemes.

The apparatus 50 comprises a current sensing circuit 52 and a readout circuit 54 that are configured to perform various operations at specific relative timings. Example timings are illustrated in the graphs of FIGS. 6 and 8, in which the horizontal axes represent time and the vertical axes represent the presence or absence of pulses representing specific functionalities. The pulses shown correspond respectively to sensing frames 62, first time windows 71, second time windows 72, readout periods 73, and further readout periods 74, each of which will be described in further detail below. FIG. 6 depicts generally which readout periods 73 and 74 are available for processing outside of the first and second time windows 71,72. FIG. 8 compares specific example timing schemes.

The current sensing circuit 52 is configured to integrate the current output by the sensor element 56 during each of a plurality of time periods which are referred to herein as sensing frames 62. In an embodiment the integration is performed using an integrating amplifier circuit 58. The sensing frames 62 optionally have a constant predetermined duration (i.e. constant horizontal length in the depiction of FIGS. 6 and 8). The integration process is stopped and reset in between each sensing frame 62 during a reset time window 64 located in between adjacent sensing frames 62. The reset operation results in the output from the integrating amplifier circuit 58 being reset to a reference value. Within each sensing frame 62 (i.e. during each sensing frame 62) the current sensing circuit 52 obtains a first analogue sample of the integral during a first time window 71 in the sensing frame 62 and a second analogue sample of the integral during a second time window 72 in the sensing frame 62, the second time window 72 being later than the first time window 71 in each sensing frame 62. In an embodiment a sample-and-hold circuit 60 is used to obtain the first and second analogue samples and to store temporarily the first and second analogue samples. In embodiments, the samples are used to perform correlated double sampling and may be referred to respectively as CDS1 and CDS2 time windows 71,72.

The readout circuit 54 is configured to process the first and second analogue samples, obtained for example from the sample-and-hold circuit 60, in order to output a digital output signal 55 representative of the current output from the sensor element 56, for example based on a difference between the first and second analogue samples, for example using a correlated double sampling (CDS) procedure. Processing by the readout circuit 54 comprises analogue to digital conversion (ADC) processing to obtain the digital output signal and output processing to output the digital output signal.

The readout circuit 54 may be implemented on a single chip (e.g. an ASIC) and the output processing may comprise outputting of the digital output signal 55 off the chip. The output processing may comprise amplification of a digital signal. Amplification of a digital signal would in general be particularly damaging to noise levels if performed during the first and second time windows 71,72. The readout circuit 54 may also be configured to perform multiplexing between outputs from different sensor elements 56.

In an embodiment, the readout circuit 54 is configured to perform all digital operations of the ADC processing exclusively during periods outside of the first and second time windows 71,72. Although operations of the ADC processing will typically be less likely to couple large amounts of noise into the samples taken in the first and second time windows 71,72, it is nevertheless desirable that at least all the digital operations of the ADC processing take place outside of the first and second time windows 71,72. The digital operations may include temporary local storage of a digital output of the ADC processing and/or transmitting of the locally stored digital output across the chip ready for the output processing (e.g. off the chip).

In an embodiment, the readout circuit 54 is configured to perform the output processing to output the digital output signal 55 for each sensing frame 62 during integration of the current output by the sensor element 56 in a later sensing frame 62, optionally in the immediately subsequent sensing frame 62. For example, in the arrangement of FIG. 6, a digital output for the leftmost sensing frame 62 (marked "A") may be provided during a later sensing frame (e.g. sensing frame "B" or "C" or later). In an embodiment, for each sensing frame 62 the readout circuit 54 is configured respectively to perform the ADC processing and the output processing in different sensing frames 62. For example, the ADC processing may be performed in a first sensing frame 62 and the output processing corresponding to that ADC processing may be performed in an immediately subsequent sensing frame 62.

Example readout periods 73, 74 (for output processing and, optionally, other processing of the readout circuit 54) that are outside of the first and second time windows 71, 72 are shown in FIG. 6. In this example readout periods 73,74 are provided both between the first and second time windows 71 and 72 within each sensing frames 62 and between the second time window 72 in each sensing frame 62 and the first time window 71 in each immediately subsequent sensing frame 62 (thereby lying within or overlapping with the reset time window 64). The addition of noise to the first and second analogue samples originated from electrical activity in the readout circuit 54 is therefore reduced or eliminated. Where it is necessary to read out large numbers of sensor elements 56 rapidly it may be desirable for the readout circuit 54 to operate at least partially within a portion of the sensing frames 62 (but outside of the first and second time windows 71 and 72), i.e. within at least the readout periods 73 in the example shown in FIG. 6, in order to provide sufficient time for the readout operations to be completed without extending the sensing frames 62 or the period in between the sensing frames 62.

Figure 13:
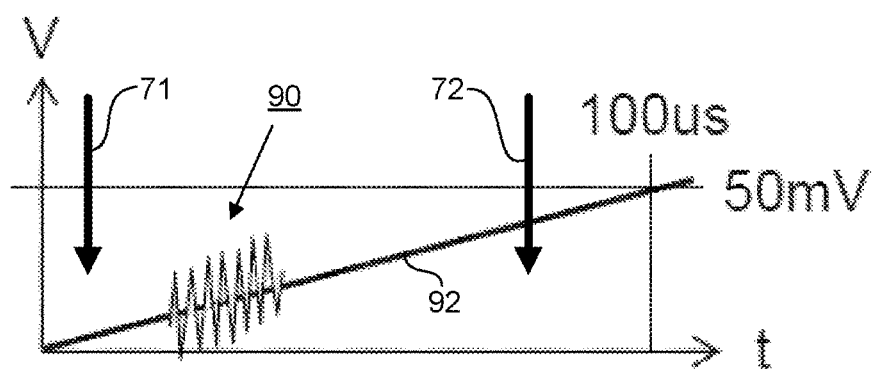
FIG. 13 is an example output from an integrating amplifier circuit of the type depicted in FIG. 12.

FIG. 13 shows an example output V from the integrating amplifier circuit 58 as a function of time, t, during typical operation of the apparatus 50 during a sensing frame 62. It can be seen that noise sources coupling to the input of the integrating amplifier circuit 58 due to processing in the readout circuit 54 generate noise 90 on the integrated output of the integrating amplifier circuit 58. The inventors have recognised that if the noise sources are periodic (which they can be arranged predominantly to be in typical applications) the disturbance disappears once it has stopped i.e. the integrated output 92 of the integrating amplifier circuit 58 continues on its original trajectory (extrapolating from the trajectory it had before the noise happened). Therefore the samples taken before and after the period influenced by the noise 90, in time windows 71 and 72, are unaffected by the noise 90. In most practical applications most noise paths to the input of the integrating amplifier circuit 58 are AC. The use of triple well silicon CMOS technology, which is known when implementing low noise ASICs, can contribute to reducing this. There is a DC noise path through the nanopore resistance which will not be removed by this technique. However in a typical application this noise contribution is 100,000 times less than the AC path (if not removed) at the maximum in a circuit bandpass of 10 kHz because the nanopore resistance is so large. This DC noise contributions is therefore considered negligible.

In an embodiment, the apparatus 50 is configured to filter the current output from the sensor element 56 before the integration processing, for example by applying a low pass filter. In embodiments of this type, noise coupling into the integration of the current output by the sensor element 56 may decay with a time constant defined by the properties of the filter. It is therefore desirable to arrange for the output processing (optionally also the digital operations of the ADC processing, optionally all operations) of the readout circuit 54 to operate exclusively not only outside of the first and second time windows 71, 72 but also outside of a period 66A starting at least one time constant of the filter (e.g. low pass filter) before the start of the first time window 71 and ending at the start of the first time window 71 and/or outside of a period 66B starting at least one time constant of the filter before the start of the second time window 72 and ending at the start of the second time window 72 (as illustrated in FIG. 6).

In an embodiment, the current sensing circuit 52 and readout circuit 54 are implemented on the same Application Specific Integrated Circuit (ASIC). This may be advantageous for the purposes of enabling processing to be performed at high speed (for example to read out data from a large number of channels). The preventing of operation of the readout circuit 54 during the first and second time windows 71,72 may be particularly beneficial in this context, where electrical components associated with the readout circuit 54 are necessarily in close proximity to electrical components associated with the current sensing circuit 52, and where noise can couple through the substrate of the ASIC.

FIGS. 6 and 8 illustrate timings for measurement of a single sensor element 56. In practice an array of sensor elements 56 may be provided, making it possible to measure multiple sensor elements 56 simultaneously. In an embodiment of this type, each of the timing schemes of FIGS. 6 and 8 may be applied in parallel to the multiple sensor elements 56. In an embodiment of this type, the outputs from multiple sensor elements 56 are integrated in parallel. Optionally, the timings shown in FIG. 6 or 8 are applied in parallel to the multiple sensor elements 56, such that one or more of the sensing frames 62, first and second windows 71, 72, and readout periods 73 and 74 occur respectively at the same times.

It can be seen that the readout periods 73 (and, to a lesser extent, the readout periods 74) can be made to be a relatively large fraction of the sensing frame 62 period. In many cases the readout periods 73, 74 will be adequately long to allow many sensor elements 56 to be measured without the need to stop detection of the current. This increases the rate at which sensor elements 56 data can be gathered relative to arrangements in which other readout arrangements are made (e.g. where data is only read out in between sensing frames 62, in the reset time windows 64. Where the sensing of molecular entities happens randomly the risk of missing the sensing of a molecular entity is reduced.

In an embodiment some digital signalling may be allowed outside of the readout periods 73 and 74. For example digital signalling for controlling the sampling in the first and second windows 71 and 72 may operate outside of the readout periods 73 and 74. Digital signalling of this nature is desirably brought onto the ASIC from an external source and is not manipulated on the ASIC itself. For example, embodiments may be provided in which no clock is provided on the ASIC (although in other embodiments a clock is provided on the ASIC). The digital signalling for controlling the sampling in the first and second time windows 71 and 72 is necessarily active at important times which may lead to some noise if counter measures are not taken. The noise can be reduced by routing the digital signalling to the sensor elements 56 using low noise fully differential current mode logic. This would be practical for this single signal, but to do this for all digital signals required on the ASIC would be undesirable for area and power reasons. Digital signalling which does not have to operate within the first and second time windows 71 and 72, such as digital signalling associated with multiplexing operations, is desirably arranged to take place outside of either or both of the first and second time windows.

In an embodiment the first and second analogue samples read out from the array of sensor elements 56 may have a random noise element resulting from amplification of current signal and noise in the integrating amplifier circuit 58. It is desirable to avoid feedback of this noise into the amplifier, which may be achieved by ensuring that these signal lines are returned to a reference voltage level after the samples have been taken. Generally it is desirable that all digital signals are returned to their starting reference states during each reset period 64, particularly the logic states of pads 124 associated with output processing blocks 126 (see FIG. 9).

FIG. 8 depicts seven example schemes for distributing the ADC processing and the output processing. In all of the examples shown, none of the periods during which the ADC processing is performed overlaps with any of the periods during which the output processing is performed. This approach avoids coupling of noise between the two processes. In scheme 1, the ADC processing and output processing are performed in a plurality of short periods interleaved in time within the readout periods 73. In scheme 2, the ADC processing is performed exclusively during the readout periods 73 and the output processing is performed exclusively during the readout periods 74. In scheme 3, the ADC processing and output processing are performed in a plurality of short periods interleaved in time within the readout periods 74. In scheme 4, the ADC processing is performed exclusively during the readout periods 74 and the output processing is performed exclusively during the readout periods 73. In scheme 5, the ADC processing is performed in a single block in each of the readout periods 73 and the output processing is performed in a different single block in each of the readout periods 73. In scheme 6, the ADC processing is performed in a period in between the reset period 64 and the first time window 71 during the readout period 74, and the output processing is performed in the readout period 73. In scheme 7, the ADC processing is performed within a single block within the readout period 73 and the output processing is performed in two separate blocks, one of which is in the readout period 74 and the other in the readout period 73 (in a different part than the single block in which the ADC processing is performed). All schemes are desirably configured such that all logic gates are at the same state when passing the first time window 71 as when passing the second time window 72. In schemes 5 and 7, where the readout period 73 contains a single ADC processing block and a single output processing block, the two blocks should be separated by a noise settling period (marked 102). A scheme obtained by combining schemes 4, 5 and 6 is also shown.

In all of the configurations shown in FIG. 8, the periods allocated for the output processing may also be used to accommodate chip input configuration signals. Chip input configuration signals may be used for example to change settings such as gain, filter, biasing, etc. Chip input configuration signals should be sent in periods outside of the first and second time windows 71,72 wherever possible and generally requires that all logic gates are at the same state when passing the first time window 71 as when passing the second time window 72.

Figure 9:
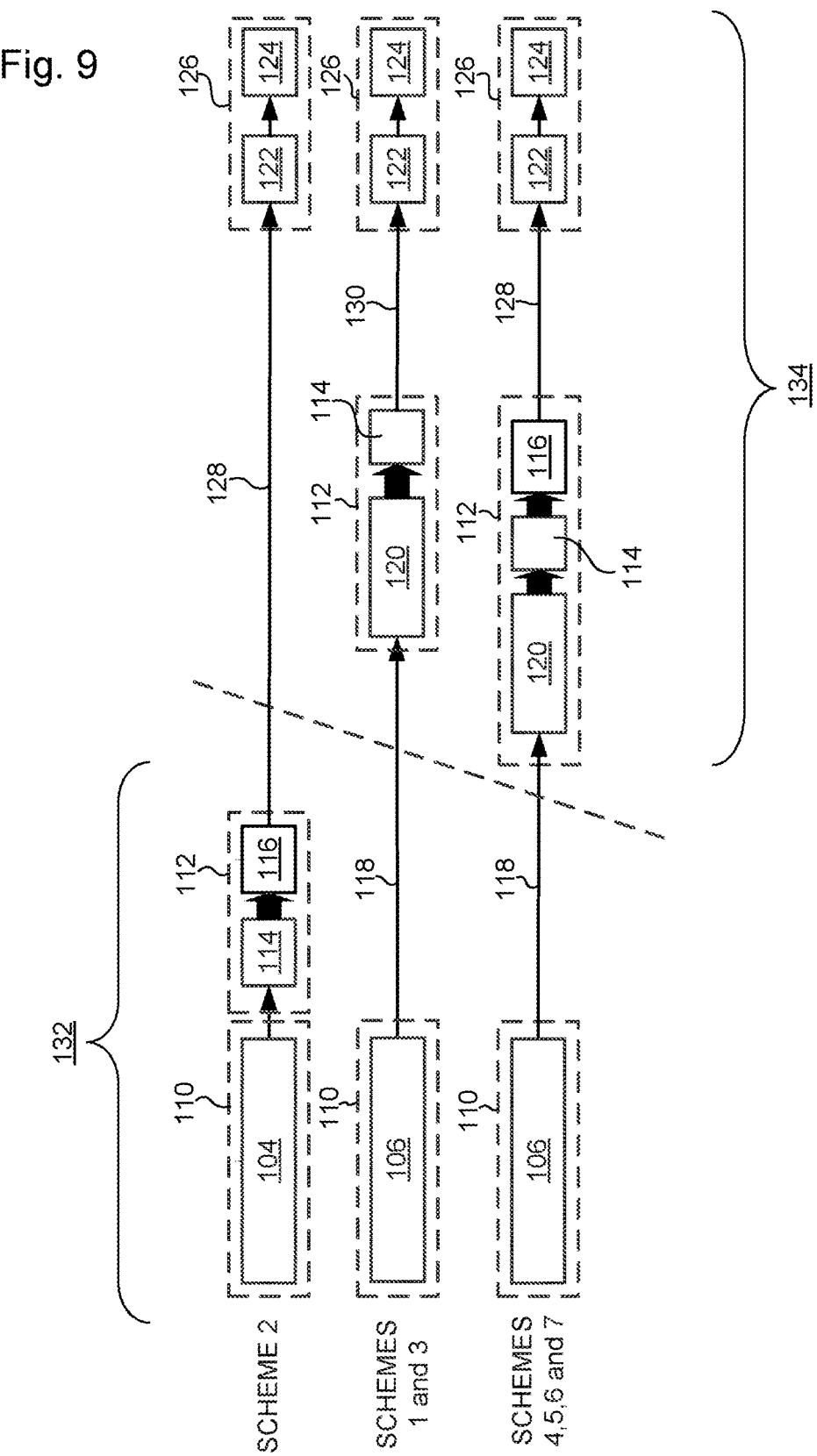
FIG. 9 depicts example chip configurations for readout circuits implementing the schemes of FIG. 8.

In embodiments the readout circuit 54 comprises circuitry for receiving current output from a plurality of different sensor elements 56 via a corresponding plurality of channels. In such embodiments the readout circuit 54 will comprise an array of individual-channel circuit elements which are each configured to handle processing for an individual one of the channels, together with one or more global circuit elements which are configured to handle processing operations for more than one (optionally all of) the channels. The processing performed by the readout circuit 54 (e.g. the ADC processing and/or the output processing) can be distributed in various ways between the individual-channel circuit elements and the global circuit elements. FIG. 9 shows example configurations for the different schemes shown in FIG. 8. Examples of individual-channel circuit elements 132 are shown on the left of the broken line. Examples of global circuit elements 134 are shown on the right of the broken line. It may be convenient to position the individual-channel circuit elements 132 in a central region of the chip and the global circuit elements 134 in peripheral regions of the chip, although this is not essential.

The individual-channel circuit elements 132 for the example configuration corresponding to scheme 2 comprises a channel block 110 and an ADC block 112. The channel block 110 comprises circuitry for providing the analogue samples from the first and second time windows 71,72. The ADC block 112 comprises circuitry 114 for performing the ADC processing. In this example, the ADC block 112 further comprises a data store for locally storing data output from the ADC processing, in order to allow delayed serial transmission of data (arrow 128) between the individual-channel circuit elements 132 and the global circuit elements responsible for the output processing.

The global circuit elements 134 for the example configuration corresponding to scheme 2 comprise an output processing block 126. The output processing block 126 comprises a pad driver 122 and a pad 124. The output processing block 126 may also be referred to as a readout pin. The pad driver 122 drives movement in the voltage state of the pad 124 in order to perform the output processing. The output processing requires relatively high power. It is therefore particularly desirable for movement of the pads 124 to occur exclusively outside of the first and second time windows 71,72 to avoid introducing noise into the current measurements.

The individual-channel circuit elements 132 for the example configuration corresponding to schemes 1 and 3 comprise a channel block 110. The channel block 110 comprises circuitry for providing the analogue samples from the first and second time windows 71,72 in a multiplexed signal. The multiplexed signal is transmitted to the global circuit elements 134 (arrow 118).

The global circuit elements 134 for the example configuration corresponding to schemes 1 and 3 comprise an ADC block 112. The ADC block 112 in this example comprises a capacitor store array 120 configured to store an array of accumulated charges from the multiplexed input signal. The ADC block 112 further comprises circuitry 114 for performing the ADC processing. Serial data output from the ADC block 112 is sent (arrow 130) to an output processing block 126. The output processing block 126 may be configured in the same way as the output processing block 126 described above with reference to the example configuration for scheme 2.

The individual-channel circuit elements 132 for the example configuration corresponding to schemes 4, 5, 6 and 7 comprise a channel block 110 configured in the same way as the channel block 110 described above with reference to the example configuration for schemes 1 and 3. The multiplexed signal is transmitted from the channel block 110 to the global circuit elements 134 (arrow 118).

The global circuit elements 134 for the example configuration corresponding to schemes 4, 5, 6 and 7 comprise an ADC block 112 comprising the same elements as the ADC block 112 described above with reference to the example configuration corresponding to schemes 1 and 3. The ADC block 112 of this example additionally comprises a data store 116 to allow delayed serial transmission of data (arrow 128) between the ADC block 112 and an output processing block 126. The output processing block 126 may be configured as described above with reference to the example configurations for schemes 1-3.

The above-described example configuration for scheme 2 facilitates achieving low noise because the ADC processing is performed locally (i.e. in the individual-channel circuit elements 132). The need to transmit data across the chip is therefore reduced, thereby facilitating avoidance of the first and second time windows 71,72 while maintaining high data throughput. The above-described example configurations for schemes 1 and 3 have the advantage of requiring less silicon because an ADC processing block 112 is not required for every channel. The above-described example configurations for schemes 4-7 combine the advantages of scheme 2 and schemes 1 and 3. Firstly, the provision of a data store 116 after the circuitry 114 for performing the ADC processing allows serial data output to the pads 124, which may require relatively high power and therefore potential contribute significantly to systematic noise, to be delayed, facilitating avoidance of such transmissions during the first and second time windows 71,72 while maintaining high data throughput. Local data stores require very low power and therefore contribute little systematic noise. Transients settle quickly for local circuits. Secondly, less silicon is needed because an ADC processing block 112 is not provided in every channel.

In embodiments, the circuitry 114 for performing the ADC processing for schemes 3-7 comprises a pipeline ADC. The pipeline ADC may for example operate between about 60 and 100 MHz with a block size of about 100. The data stores 116 may be implemented using a shift register (e.g. 11-bit per channel).

In embodiments, the circuit 114 for performing the ADC processing for scheme 1 or scheme 2 comprises a Successive Approximation Register (SAR) ADC.

Schemes 2 and 4-7 all allow a delay in transmission of data to the pads 124. This facilitates avoidance of any pad movement during or near the first and second time windows 71,72, thereby avoiding systematic noise being input to the current measurements by pad movement.

It is desirable that all logic states of the pads 124 are in the same state during both of the first and second time windows 71,72.

In an embodiment, the current measuring apparatus 50 is used in molecular entity sensing apparatus in order to determine a characteristic of an analyte. The sensing apparatus comprises a sensor device comprising an array of sensor elements 56. Each of the sensor elements 56 of the sensor device is arranged to output an electrical current that is dependent on a physical phenomenon that is dependent on the molecular entity being sensed. In an embodiment a plurality of the current measuring apparatuses 50 are used. In such an embodiment each of the current measuring apparatuses 50 is configured to measure the electrical current output by one or more of the sensor elements 56 and provide a digital output signal 55 representing the current output by the one or more of the sensor elements 56.

In an embodiment the physical phenomenon is a stochastic event. In an embodiment the stochastic event is an interaction between a molecular entity and the sensor element 56. In an embodiment each of the sensor elements 56 comprises a membrane comprising an ion channel. The ion channel may be for example a biological pore, for example a transmembrane protein pore. In an embodiment the sensor elements 56 are each arranged to support an amphiphilic membrane in which a membrane protein is capable of insertion, the physical phenomena being an interaction of a molecular entity with a membrane protein in an amphiphilic membrane.

The analyte to be determined may be polymeric such as an amino acid, peptide, polypeptide, a protein or a polynucleotide. The polynucleotide may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art. The analyte to be determined may be an amptamer. The molecular entity is caused to translocate the pore and the interactions between the molecular entity and the pore measured.

Translocation of the analyte through the pore may be assisted by a motor protein such as a polynucleotide handling enzyme. Preferred enzymes are polymerases, exonucleases, helicases and topoisomerases, such as gyrases. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561). Alternatively translocation of the analyte through the pore may also be assisted by voltage control, such as disclosed by International Patent Application PCTTT/US2008/004467.

The characteristic to be determined may be a sequence characteristic of the polymer. Determination of a sequence characteristic may be carried out by methods disclosed by International Patent Applications PCT/GB2012/052343 and PCT/GB2013/050381.

The biological pore may be a naturally occurring pore or may be a mutant pore. Further, a biological nanopore may be a transmembrane protein pore. Typical pores are described in U.S. Patent Application No. 2012/1007802, and are described in Stoddart D et al., Proc Natl Acad Sci, 12;106 (19):7702-7, Stoddart D et al., Angew Chem Int Ed Engl. 2010;49(3):556-9, Stoddart D et al., Nano Lett. 2010 Sep 8;10(9):3633-7, Butler TZ et al., Proc Natl Acad Sci 2008; 105(52):20647-52, U.S. Patent Application Publication 2014/186823 and WO2013/153359, all of which are hereby incorporated by reference. The pore may be homo-oligomeric, namely, derived from identical monomers. The pore may be hetero-oligomeric, namely where at least one monomer differs from the others. The pore may be a DNA origami pore, as described by Langecker et al., Science, 2012; 338: 932-936, hereby incorporated by reference.

The biological pore may be provided within a membrane amphiphilic layer (also referred to as an amphiphilic membrane). An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed by, Gonzalez-Perez et al., Langmuir, 2009, 25, 10447-10450, and U.S. Pat. No 6,723,814, both hereby incorporated by reference. The polymer may be a PMOXA-PDMS-PMOXA triblock copolymer.

In another embodiment, the membrane is a solid state layer comprising one or more apertures. The support structure can be formed from either or both organic and inorganic materials, including, but not limited to, microelectronic materials, whether electrically conducting, electrically semiconducting, or electrically insulating, including materials such as II-IV and III-V materials, oxides and nitrides, like Si3N4, Al2O3, and SiO, organic and inorganic polymers such as polyamide, plastics such as Teflon®, or elastomers such as two-component addition-cure silicone rubber, and glasses. A solid state support structure may be formed from monatomic layers, such as graphene, or layers that are only a few atoms thick such as those disclosed in U.S. Pat. No. 8,698,481, and U.S. Patent Application Publication 2014/174927, both hereby incorporated by reference. More than one support layer material can be included, such as more than one graphene layer, as disclosed in US Patent Application Publication 2013/309776, incorporated herein by reference. Suitable silicon nitride membranes are disclosed in U.S. Pat. No. 6,627,067, and the support structure may be chemically functionalized, such as disclosed in U.S. Patent Application Publication 2011/053284, both hereby incorporated by reference.

In a further embodiment, a biological nanopore may be provided within a solid state aperture. Such a structure is disclosed for example in U.S. Pat. No. 8,828,211, hereby incorporated by reference.

In a further embodiment the invention provides a current measuring method in order to determine a characteristic of an analyte.

Methods of embodiments of the invention involve the measuring of a current passing through the pore as the analyte moves with respect to the pore. Suitable conditions for measuring ionic currents through transmembrane protein pores are known in the art. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed below, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed below, the buffer is present in the aqueous solution in the chamber. Any buffer may be used. Typically, the buffer is phosphate buffer.

In an embodiment each sensing element 56 comprises a respective electrode that is arranged to output the electric current dependent on a physical phenomenon associated with the sensing element 56. In an example of such an embodiment the sensor device further comprises a common electrode common to all the sensor elements.

A detailed example illustrating one way in which some of the features discussed above can be combined is discussed below with reference to FIG. 10-12.

Figure 10:
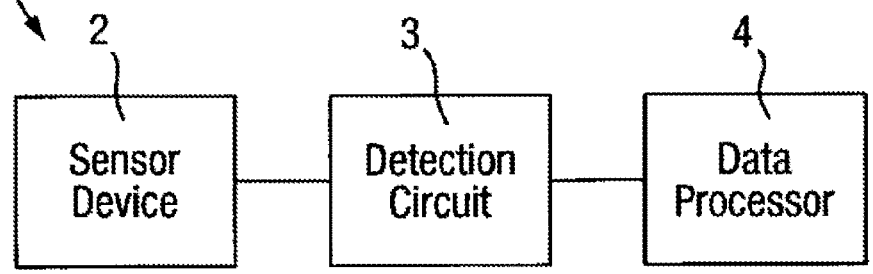
FIG. 10 is a schematic depiction of a system for sensing interactions of molecular entities with membrane proteins inserted in amphiphilic membranes.
Figure 11:
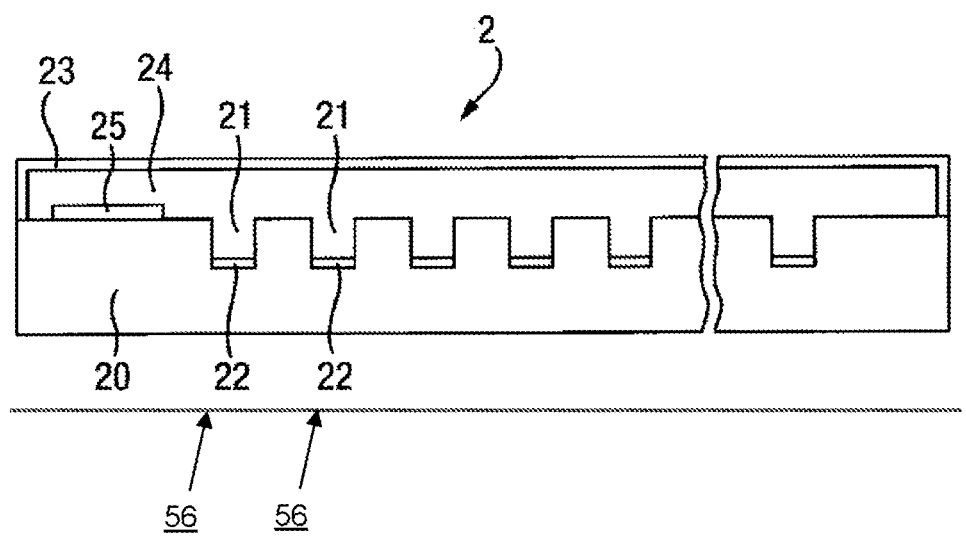
FIG. 11 is a schematic depiction of a sensor device for use with the system of FIG. 10.

A system 1 for sensing interactions of molecular entities with membrane proteins inserted in amphiphilic membranes is shown schematically in FIG. 10. The system 1 comprises a sensor device 2 connected to a detection circuit 3. The detection circuit 3 is connected to a data processor 4. The detection circuit 3 comprises elements corresponding to the current measuring apparatus 50 discussed above with reference to FIG. 6-9.

In an embodiment the sensor device 2 is an apparatus as described in detail in International Patent Application No. PCT/GB08/004127 which is incorporated herein by reference. Without limitation to the generality of the teaching therein, the sensor device 2 of this type has a construction as shown in cross-section in FIG. 11 comprising a body 20 in which there is formed a plurality of wells 21 each being a recess having a well electrode 22 arranged therein. A large number of wells 21 is provided to optimise the data collection rate of the apparatus 1. In general, there may be any number of wells 21, typically 256 or 1024, although only a few of the wells 21 are shown in FIG. 11.

Each well 21 and corresponding well electrode 22 is an example of a sensor element 56 as discussed above with reference to FIG. 6-9.

In this embodiment the body 20 is covered by a cover 23 that extends over the body 20 and is hollow to define a chamber 24 into which each of the wells 21 opens. A common electrode 25 is disposed within the chamber 23.

The sensor device 2 is prepared to form an amphiphilic membrane 26 across each well 21 and to insert membrane proteins into the amphiphilic membrane 26. This preparation may be achieved using the techniques and materials described in detail in International Patent Application No. PCT/GB08/004127, which may be summarized as follows. Aqueous solution is introduced into the chamber 24 to form the amphiphilic membrane 26 across each well 21 separating aqueous solution in the well 21 from the remaining volume of aqueous solution in the chamber 24. Membrane proteins are provided into the aqueous solution, for example by being introduced into the aqueous solution before or after that is introduced into the chamber 24 or by being deposited on an internal surface of the chamber 24. The membrane proteins spontaneously insert from the aqueous solution into the amphiphilic membranes 26. Such spontaneous insertion is a dynamic process and so there is a statistical variation in the number of membrane proteins inserted into individual amphiphilic membranes, typically having a Poisson distribution.

Other sensor devices suitable for use in the invention are disclosed in International Patent Application No. PCT/GB2013/052776.

In respect of any given well 21, when an amphiphilic membrane 26 has been formed and a membrane protein is inserted therein, then the well 21 is capable of being used as part of a sensor element 56 that is configured to sense interactions between molecular entities and the membrane protein. These interactions are stochastic physical events. The output electrical signal across the amphiphilic membrane 26 is dependent on the interactions in the sense that the interactions cause characteristic changes in the output electrical signal. For example in the case that the membrane protein is a protein pore, then there will typically be interactions between the protein pore and a particular molecular entity (analyte) that modulate the flow of ions through the pore. The modulation of the flow of ions through the pore creates a characteristic change in current flow through the pore. The molecular entity may be a molecule or part of a molecule, for example a DNA base. Such interactions are typically very brief, requiring a high time resolution and continuous monitoring if it is desired to detect each interaction.

Figure 12:
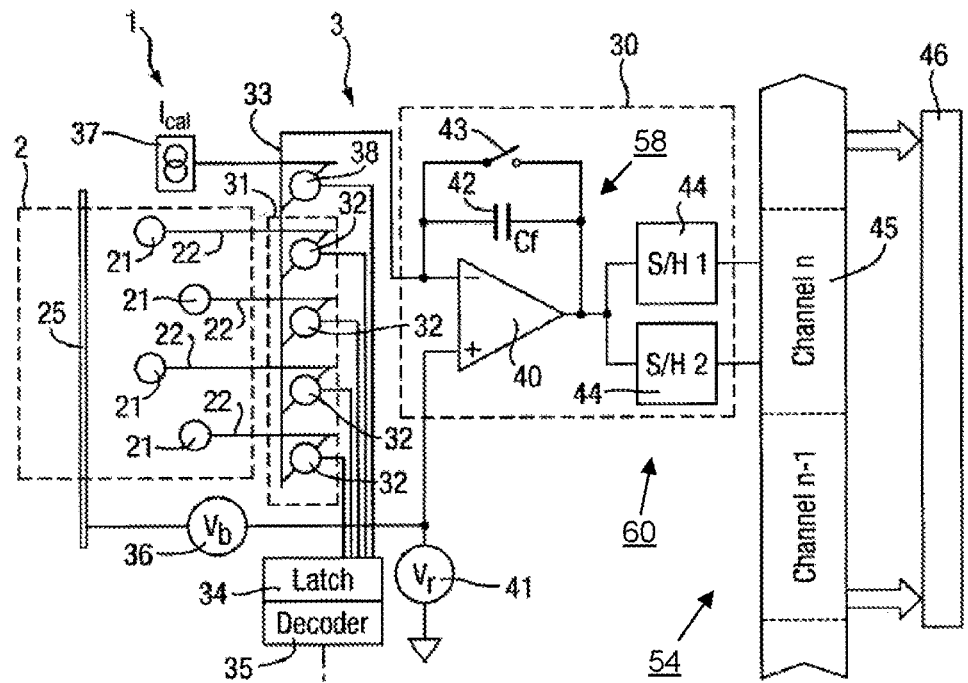
FIG. 12 is a schematic depiction of a detection circuit for use with the system of FIG. 10.

An example of a detection circuit 3 is shown in FIG. 12, wherein the sensor device 2 is shown schematically. In this embodiment the wells 21 are provided in groups. In FIG. 12, each group consists of four wells 21. In other embodiments the groups may comprise a different number of wells 21. The detection circuit 3 has a detection channel 30 associated with each group of wells 21. For clarity, FIG. 12 shows a single group of wells 21 and a single detection channel 30, but typically there are plural groups of wells 21 each with an associated detection channel 30 arranged as shown in FIG. 12. For example, for some applications, the sensor device 2 might comprise a total of 4096 wells 21 and 1024 detection channels 30.

In this embodiment, the system 1 further includes a switch arrangement 31 which is capable of selectively connecting the detection channel 30 to any one of the wells 21 in the group. In particular, the switch arrangement 31 is a 1-to-4 multiplexor (in general a 1-to-N multiplexor where N is the number of wells 21 in the group), comprising four switches 32 each connected between the well electrode 22 of one of the wells 21 and a common contact 33 which is itself connected to the input of the detection channel 30 (current sensing circuit 52).

The switches 32 may in principle be any type of analogue switch, but are preferably semiconductor switches, for example formed by transistors, preferably field effect transistors. The switches 32 are selected to provide minimal leakage to the detection channel 30 either from the wells 21 that are not connected through switches 32 that are open or from the latch 34 through the switches 32. In an embodiment, dynamic charge injection effects are avoided by running the apparatus 1 with the switches in a static configuration for most of the time.

In an embodiment, the state of the switch arrangement 31 is controlled by data stored in a digital latch 34 controlled by decoder logic 35. The decoder logic controls the latch 34 in accordance with a control signal received by the decoder logic 35 so that any one single switch 32 is closed at a time, thereby connecting the corresponding well 21 to the detection channel 30. The decoder logic 35 allows the switch arrangement 31 in respect of each group of wells 21 to be switched without affecting the state of the switch arrangement 31 in respect of any other group.

There may be no requirement to be able to change the configuration of the switch arrangement 31 rapidly. In a typical embodiment, changes are required on a time scale of minutes and a complete update is achievable on a timescale of up to 0.1 s to 1 s. In such an embodiment it is acceptable to implement the latch 34 as a shift register and to implement a serial data interface for the decoder logic 35, optionally utilizing differential signalling.

In this embodiment the wells 21 are biased with respect to the input of the detection channel 30 by a bias supply 36 connected to the common electrode 35. Typically the bias voltage is up to 200 mV.

In an embodiment, any well 21 which is not actively connected to the detection channel 30 is allowed to float to the potential of the common electrode 25 via the fluid in the well 21 and will therefore pass no current. This eliminates the potential for amplifier saturation by wells 21 which have no amphiphilic membrane 26. The decoder logic 35 may also control the latch 34 to provide a state in which all of the switches 32 open, thus allowing all the wells 21 in the group to float. In this state, the detection channel 30 has no input current, and none of the wells 21 passes any current either.

To reduce costs, in an embodiment the detection circuit 3 is implemented in a semiconductor chip provided separately from the sensor device 2. In other embodiments, one or more components of the detection circuit 3, for example the switch arrangement 31, latch 34 and decoder logic 35, are provided in a separate semiconductor chip integrated into the sensor device 2. This approach reduces interconnection requirements, but may require the sensor device 2 to have a few extra digital control lines to supply the control signal to the decoder logic 35. Optionally, the detection circuit 3 is arranged as follows to supply a calibration current of known magnitude, equivalent to the current passed by a working well 21, typically of magnitude 50 pA to 100 pA, to the detection channel 30 for testing purposes so that the functionality of the detection circuit 3 can be assured prior to the introduction of any chemistry. The detection circuit 3 includes a calibration source 37 that is operable to supply the calibration current and a further switch 38 connected between the calibration source 37 and the common contact 33. The further switch 38 is controlled by the latch 34 and the decoder logic 35 in the same manner as the switch arrangement 31 to allow connection of the calibration source 37 to the detection channel 30, instead of any of the wells 21.

In this embodiment each detection channel 30 is arranged as follows to amplify the electrical signals from a well 21 that is connected thereto by the switch arrangement 31. The detection channel 30 is therefore designed to amplify very small currents with sufficient resolution to detect the characteristic changes caused by the interaction of interest. The detection channel 30 is also designed with a sufficiently high bandwidth to provide the time resolution needed to detect each such interaction.

The detection channel 30 comprises an integrating amplifier circuit 58 (corresponding to the integrating amplifier circuit 58 referred to above with reference to FIG. 6-9). In this embodiment, the integrating amplifier circuit 58 includes a charge amplifier 40. The charge amplifier 40 is a differential amplifier having: an inverting input which constitutes the input of the detection channel 30 and is connected to the common contact 33; and a non-inverting input that is connected to an internal reference source 41. The bias source 36 is connected between the common electrode 25 of the sensor device 2 and the non-inverting input of the charge amplifier 40 to apply the bias voltage therebetween.

The charge amplifier 40 is arranged to operate as an integrating amplifier circuit 58 by means of a capacitor 42 being connected between the inverting input of the charge amplifier 40 and the output of the charge amplifier 40. A control switch 43 is connected in parallel with the capacitor 42 to control the integration performed by the charge amplifier 40. The integrating amplifier circuit 58 integrates the current supplied thereto from the well 21 in each sensing frame 62 to provide an output representative of the charge supplied between the first and second time windows 71 and 72 in which analogue samples of the integration are taken. The sensing frames 62 are chosen to be short enough to provide sufficient time resolution to monitor events of interest occurring in the well 21.

The output of the charge amplifier 40 (and integrating amplifier circuit 58) is connected to a sample-and-hold circuit 60. In this embodiment, the sample-and-hold circuit 60 comprises two sample-and-hold amplifiers 44 arranged in parallel and optionally provided with voltage gain. In use, the sample-and-hold amplifiers 44 are operated to provide correlated double sampling by each being switched synchronously with the control switch 43 to sample and hold the output of the charge amplifier 40 respectively during the first and second time windows 71 and 72. The useful signal is derived by taking differences between the two outputs of the sample-hold amplifiers 44. The sampling rate is sufficiently high to time resolve the output signals. In this embodiment, the amplified signals output by the sample-and-hold amplifiers 44 are supplied to a multiplexor 45. The multiplexor 45 multiplexes the amplified signals output by all the detection channels 30 and supplies them to the data processor 4. In an embodiment the multiplexor 45 comprises a shift register connected to the data processor 4 through an A/D convertor 46. In other embodiments the multiplexor 45 takes other suitable forms, for example including being a digital device with A/D conversion occurring between the sample-and-hold amplifiers 44 and the multiplexor 45.

The multiplexor 45 and A/D converter 46 are examples of components forming part of a readout circuit 54, as described above with reference to FIGS. 6 and 7. The readout circuit 54 may comprise different elements or alternative elements.

In an alternative embodiment each detection channel 30 is provided with two charge amplifiers arranged in parallel and used alternately to provide greater efficiency by each charge amplifier being reset whilst the other charge amplifier is performing integration.

It is occasionally necessary to unblock a membrane protein that is a protein pore, by inverting the potential applied across the well 21 via the common electrode 25. For this to be effective, the input to the charge amplifier 40 is designed to remain at a constant bias potential even when presented with a negative current (of similar magnitude to the normal current, typically of magnitude 50 pA to 100 pA).

The data processor 4 receives and processes the signals from each detection channel 30 output from the detection circuit 3. The data processor 4 stores and processes the amplified signals. The data processor 4 optionally comprises one or more components that form part or all of the readout circuit 54.

In an embodiment the data processor 4 also controls the operation of the detection circuit 3 and acts as a switching controller for the switch arrangement 31 by supplying the control signal to the decoder circuit 35. The data processor 4 may be a microprocessor running an appropriate program or may include dedicated hardware. The data processor 4 may comprise a card to be plugged into a computer such as a desktop or laptop. Such a computer may include graphics tools for displaying the amplified signals to the user, and may also provide analysis of the amplified signals depending on the interaction of interest.

In operation, in an embodiment the data processor 4 monitors the amplified signals output by each detection channel 30 and controls the switch arrangement 31 on the basis thereof. In particular, the data processor 4 controls the switch arrangement 31 to connect the detection channel 30 to one of the wells 21 which has acceptable quality of performance, i.e. in this example meaning that there an amphiphilic membrane 26 is formed across the amphiphilic membrane with a single membrane protein inserted therein. This may be achieved by analysing the amplified signals to detect signals that are characteristic of the physical state of the well 21, for example using the analysis techniques disclosed in WO 2008/102120 (International Patent Application No. PCT/GB08/000562) which is incorporated herein by reference.

The apparatus 1 described above is designed to sense a physical phenomenon which is an interaction of a molecular entity with a membrane protein in an amphiphilic membrane 26. However the advantages achieved thereby are equally applicable to sensing other physical phenomenon using sensor elements. For example similar advantages are achieved in an apparatus for sensing of other types of interaction of a molecular entity, and/or other types of physical event, by an array of sensor elements arranged to sense occurrences of the physical event by outputting an electrical signal at an electrode that is dependent on those occurrences. Similar advantages are achieved in an apparatus for sensing using sensor elements which each comprise a respective well formed in a substrate and within which are arranged the respective electrodes.

The features defined in the claims may be used together in any combination.

The invention claimed is:

1. A current measuring apparatus for measuring an electrical current output by a sensor element, the current measuring apparatus comprising:
   a current sensing circuit configured to integrate the current output by the sensor element during each of a plurality of sensing frames and, in each sensing frame, to obtain a first analogue sample of the integral during a first time window in the sensing frame and a second analogue sample of the integral during a second time window in the sensing frame, the second time window being later than the first time window in each sensing frame; and
   a readout circuit configured to process the first and second analogue samples in order to output a digital output signal representing the current output by the sensor element between the first and second time windows in each sensing frame, the processing comprising analogue to digital conversion processing to obtain the digital output signal and output processing to output the digital output signal, wherein:

the readout circuit is configured to perform the output processing exclusively during periods outside of the first and second time windows.

2. The apparatus of claim 1, wherein the readout circuit is configured to perform all digital operations of the analogue to digital conversion processing exclusively during periods outside of the first and second time windows.

3. The apparatus of claim 1, wherein the readout circuit is configured to operate exclusively during periods outside of the first and second time windows.

4. The apparatus of claim 1, wherein the readout circuit is configured to perform a portion or all of one or more of the following during one or more of the sensing frames: the output processing, all digital operations of the analogue to digital conversion processing, all operations of the readout circuit.

5. The apparatus of claim 1, wherein in respect of the current output by the sensor element in each sensing frame the readout circuit is configured to perform the output processing during one or more periods outside of that sensing frame.

6. The apparatus of claim 5, wherein the one or more periods outside of that sensing frame comprise a period during integration of the current output by the sensor element in one or more later sensing frames.

7. The apparatus of claim 1, wherein in respect of the current output by the sensor element in each sensing frame the readout circuit is configured respectively to perform the analogue to digital conversion processing and the output processing in different sensing frames.

8. The apparatus of claim 1, wherein the readout circuit is configured to perform at least a portion of the output processing during a reset period in which the integration of the current output by the sensor element is reset.

9. The apparatus of claim 1 comprising an array of sensor elements.

10. The apparatus of claim 1, wherein the current sensing circuit and readout circuit are implemented on the same Application Specific Integrated Circuit.

11. The apparatus of claim 1, wherein the current sensing circuit comprises an integrated amplifier circuit and a sample-and-hold circuit connected to the output of the integrating amplifier circuit.

12. The apparatus of claim 11, wherein the readout circuit is configured to extract the first and second analogue samples from the sample-and-hold circuit.

13. The apparatus of claim 1, wherein the readout circuit is configured to perform multiplexing between outputs from different sensor elements.

14. The apparatus of claim 1, wherein the apparatus is configured to apply a low pass filter to the integrated current.

15. The apparatus of claim 14, wherein the readout circuit is configured to perform the output processing exclusively during periods outside of the first and second time windows in each sensing frame and outside of periods starting at least one time constant of the low pass filter before the start of each time window and ending at the start of each time window.

16. A molecular entity sensing apparatus comprising:
a sensor device comprising an array of sensor elements, each sensor element being arranged to output an electrical current that is dependent on an interaction between a molecular entity and the sensor element; and
a plurality of the current measuring apparatus of claim 1, wherein each current measuring apparatus is configured to measure the electrical current output by one or more of the sensor elements and provide a digital output signal dependent on the current output by the one or more of the sensor elements.

17. The apparatus of claim 16, wherein each sensing element comprises a respective electrode that is arranged to output the electric current dependent on the interaction between the molecular entity and the sensor element, and the sensor device further comprises a common electrode common to all the sensor elements.

18. The apparatus of claim 16, wherein each of the sensor elements comprises an ion channel, wherein the ion channel is a membrane protein.

19. The apparatus of claim 16, wherein the sensor elements are each arranged to support an amphiphilic membrane in which a membrane protein is capable of insertion, and the interaction between the molecular entity and the sensor element is an interaction between the molecular entity and the membrane protein in the amphiphilic membrane.

20. A current measuring method for measuring an electrical current output by a sensor element, the method comprising:
integrating the current output by the sensor element during each of a plurality of sensing frames and, in each sensing frame, obtaining a first analogue sample of the integral during a first time window in the sensing frame and a second analogue sample of the integral during a second time window in the sensing frame, the second time window being later than the first time window in each sensing frame; and
processing the first and second analogue samples to output a digital output signal representing the current output by the sensor element between the first and second time windows in each sensing frame, the processing comprising analogue to digital conversion processing to obtain the digital output signal and output processing to output the digital output signal, wherein:
the output processing is performed exclusively during periods outside of the first and second time windows.

21. The method of claim 20, wherein the output processing for each frame is performed during an immediately subsequent sensing frame.

22. The method of claim 20, wherein the method comprises applying correlated double sampling to the current output by the sensor element using the first and second analogue samples.

23. A molecular entity sensing method, the method comprising:
providing a sensor device comprising an array of sensor elements, each sensor element being arranged to output an electrical current that is dependent on an interaction between a molecular entity and the sensor element; and
using the method of claim 20 to measure the electrical current output by one or more of the sensor elements and provide a digital output signal dependent on the current output by the one or more of the sensor elements.

* * * * *